United States Patent [19]

Engen

[11] Patent Number: 5,121,742
[45] Date of Patent: Jun. 16, 1992

[54] LOWER EXTREMITY ORTHOTIC DEVICE

[75] Inventor: Thorkild J. Engen, Houston, Tex.

[73] Assignee: Baylor College of Medicine, Houston, Tex.

[21] Appl. No.: 428,357

[22] Filed: Oct. 27, 1989

[51] Int. Cl.⁵ .............................................. A61F 5/00
[52] U.S. Cl. ...................................... 602/16; 623/26; 602/26; 602/27
[58] Field of Search ............. 623/26; 128/80 R, 80 C, 128/80 F, 80 G, 80 M, 87 R, 89 R, 90

[56] References Cited

U.S. PATENT DOCUMENTS

| 2,522,853 | 9/1950 | Black ..................................... 623/26 |
| 3,230,952 | 1/1966 | Terron . |
| 3,581,741 | 6/1971 | Roseman et al. .................. 128/80 C |
| 4,353,361 | 10/1982 | Foster . |
| 4,494,534 | 1/1985 | Hutson ............................... 128/80 F |
| 4,602,627 | 7/1986 | Vito et al. . |
| 4,688,559 | 8/1987 | Vito et al. . |
| 4,776,326 | 10/1988 | Young et al. . |

FOREIGN PATENT DOCUMENTS 0195186 9/1986 European Pat. Off. .
2101894 1/1983 United Kingdom .

OTHER PUBLICATIONS

"The TIRR Polypropylene Orthosis", T. J. Engen, Orthotics and Prosthetics, vol. 26, No. 4, 1972.
"Accomplishments in Modern Orthotic Patient Management-Indications for the Future," T. J. Engen, Journal of the American Orthotic and Prosthetic Association, vol. 33, No. 3, 1979.
"Lower Extremity Orthotics", Engen et al., Current Orthopaedics, vol. 3, 194-200, 1989.
"Lightweight Modular Orthosis", T. Engen, Prosthetics and Orthotics International, vol. 13, 125-129, 1989.
"TIRR Physician Gets Award for Leg Brace", Texas Medical Center News, vol. 12, No. 1, Jan. 1990.

Primary Examiner—Richard J. Apley
Assistant Examiner—Linda C. M. Dvorak
Attorney, Agent, or Firm—Weil, Gotshal & Manges

[57] ABSTRACT

Modular components of a lower extremity orthotic device are fitted to a patient and assembled at once. The components include thermoplastic inner and outer side members and a thermoplastic ankle foot orthotic member for a standing frame lower extremity orthotic device. To allow patient pivotal knee rotation, knee joints and means for operating knee joints are interspaced between thigh and calf side members.

12 Claims, 11 Drawing Sheets

LOWER EXTREMITY ORTHOTIC DEVICE

This invention relates to orthotics devices and in particular to a lightweight, modular, orthosis which is readily and inexpensively manufactured.

BACKGROUND OF THE INVENTION

Clinical experience of the last 45 years has indicated that patients with paraplegia can learn to stand and ambulate with suitable orthotic assistance. Patients with paralysis of muscles innervated from the sacral to the middle thoracic segments of the spinal cord can be provided with means to stabilize the joints of the lower extremities which allows the patient to perform a variety of functional activities.

Thus, the use of orthotic devices to help support and control joints of the lower extremities following muscle paralysis is an important part of medical rehabilitation. However, the development of lower extremity orthotic devices has experienced few major breakthroughs in the past twenty five years. Conventional orthotic devices are awkward and cumbersome, particularly for the patient with generalized motor weaknesses. Moreover, these devices are exceedingly heavy, unattractive and must be permanently attached to the wearer's shoes. Furthermore, they tend to cause damage to clothing due to frictional wear, rough metal edges, and pinching joints.

Typically, one of four basic types of conventional lower extremity orthotic devices are prescribed for patients with various diagnostic problems resulting in unilateral paralysis, asymmetrical bilateral paralysis or total paralysis of the lower extremities: 1) a short leg brace known as an ankle-foot-orthosis (AFO), which has an adjustable, spring loaded ankle joint (Klenzak type); 2) a long-leg brace known as a knee-ankle-foot orthosis (KAFO), which has a free ankle joint and shoe modification; 3) a KAFO with an adjustable, spring-loaded ankle joint; and 4) a KAFO with controlled knee, free ankle motions and ischial weight-bearing support. Each of these conventional orthoses incorporates a permanent shoe-brace attachment.

For example, the Scott-Craig orthosis, a category (4) KAFO is most often prescribed for patients suffering injuries ranging from the sacral to the middle thoracic segments of the spinal cord (Lehmann et al. Phys. Arch. Med. Rehabil. 57: 438-442, 1976). These devices are long-leg braces with knee locks that are made of metal to withstand heavy-duty use.

Typically, a shoe base is constructed to provide a foundation upon which a pair of upright metal struts are attached by way of an ankle joint, and, traditionally, the shoe takes the form of a sole plate. However, these braces have significant drawbacks in that they are cumbersome, heavy, difficult to fit and adjust, difficult to apply and remove, and also very expensive. The cost of such braces, as well as the length of time required for their production, is significantly increased by the fact that they must be custom-made by an orthotist working with measurements taken from the individual patient. Even under ideal conditions, the period of time from when the braces are ordered to receipt by the patient typically requires several weeks. This produces the undesirable result of not having the braces available for use by the patient early in a rehabilitation program when, for trophic and psychological reasons, they are needed most to support standing. By the time they are finally fitted and in use by the patient, insufficient time may remain for adequate practice in using them. Consequently, these expensive appliances are often set aside within a few months after the patient leaves the hospital and thereafter, used very infrequently if at all (Priestly and Lehmkuhl, Phys. Ther. 62:660, 1982).

Moreover, since most conventional metal orthoses provide the wearer with, in a sense, an exoskeletal system to achieve the purposes of standing and limited ambulation, they do not utilize the patient's normal skeletal structure to carry a part of weight-bearing loads, even though it may be capable of carrying part or all of the body weight. The end result is braces that are too heavy and bulky to permit sufficient utilization of any residual motor functions that might be present.

Another drawback of conventional lower extremity orthoses is that the knee joints of such devices correspond poorly with the polycentric joint of the human knee, often resulting in an undesirable sliding motion when the patient walks, sits or stands. This undesirable motion can also lead to excessive wear and tear of clothing.

When new plastic materials became available, they were recognized as suitable replacements for the steel, aluminum and other metals formerly used to construct orthotic devices. The use of plastics in orthotics allowed orthotists to consider new design concepts, resulting in lighter and more cosmetically acceptable devices. For example, research at the Texas Institute for Rehabilitation and Research (TIRR) by the present inventor led to the development of a molded polypropylene ankle-foot orthotic device (AFO) which is worn inside the shoe. This AFO eliminated the mechanical ankle joint and brace shoe attachment of conventional braces and allowed the user the freedom to wear the device with his or her own shoe. (Engen, Orthotics and Prosthetics 26(4):1-15, 1972).

It was found, however, that AFO's constructed of unreinforced polypropylene were too flexible to provide sufficient dorsiflexion assistance. Therefore, corrugations were introduced into the molded AFO to strengthen those portions of the brace subjected to the greatest stress. The polypropylene AFO has an advantage in that it can be mass-manufactured and is modifiable after fabrication to ensure a proper fit.

In order to eliminate the drawbacks of conventional lower extremity orthotic devices, heretofore, there existed a need to incorporate the AFO into a structurally sound yet lightweight long-leg brace that is inexpensive to manufacturer and could be readily adapted to fit the user.

In accordance with the present invention, the lower extremity orthotic device has become even more lightweight, provides for an easier fit for the patient in a shorter amount of time, and enables the patient to manipulate the knee joints in a much easier fashion. It is also much less expensive, and is resistant to salt corrosion and sand so that a patient is less restricted in his or her outdoor activities.

SUMMARY OF THE INVENTION

It is, therefore, an object of the present invention to provide a transitional lower extremity orthotic device for support of standing and limited ambulation during the early stages of rehabilitation of patients with paraplegia.

It is further object of the invention to provide such an orthotic device which is lightweight and which can be readily made to provide a safe and proper fit for the wearer.

It is further object of invention to provide an orthotic device which can be custom-fit to the wearer in a short amount of time and at modest expense.

It is still further object of the invention to provide a knee-ankle-foot orthosis which can be assembled from modular components using simple tools and with a minimum amount of craftsmanship.

It is a still further object of the invention to provide a modular knee-ankle-foot orthotic device which eliminates undesirable motion exhibited by conventional devices and which utilizes the patient's ability to carry a weight-bearing load.

It is a further object of the invention to provide a modular knee-ankle-foot orthosis which employs side support members constructed of lightweight, strong and semithermoplastic material and which can be incorporated into a device which has no mechanical knee joint.

It is further object of the invention to provide a modular knee-ankle-foot orthotic device incorporating a novel streamlined knee joint which overcomes the drawbacks of the prior art locking knee joints.

In accordance with the present invention, there is provided a modular orthotic device having lightweight, thermoplastic support members in confirmation with a custom fitted calf-ankle-foot orthotic member and for fastening means interconnecting these modular elements to a thigh cuff and, in one preferred embodiment, to a novel knee joint mechanism. The present invention overcomes the aforedescribed drawbacks of the prior art and various deficiencies of lower conventional extremity orthotic devices currently available to paraplegic patients. In particular, the invention encompasses improvements in the material used in the construction of such devices, as well as in the knee joint/lock mechanism and means to control movement associated with the knee joint.

BRIEF DESCRIPTION OF THE DRAWINGS

FIG. 4 (a) is a cross-sectional view of a side member used in the present invention;

FIG. 13 (a) is a cross sectional view of a position of the knee joint shown in FIG. 13;

FIG. 14 is a front internal view partly in section of a knee joint in an unlocked position attached to a side member as used in the embodiment shown in FIG. 10.

DETAILED DESCRIPTION OF THE PREFERRED EMBODIMENTS

Figure 1:
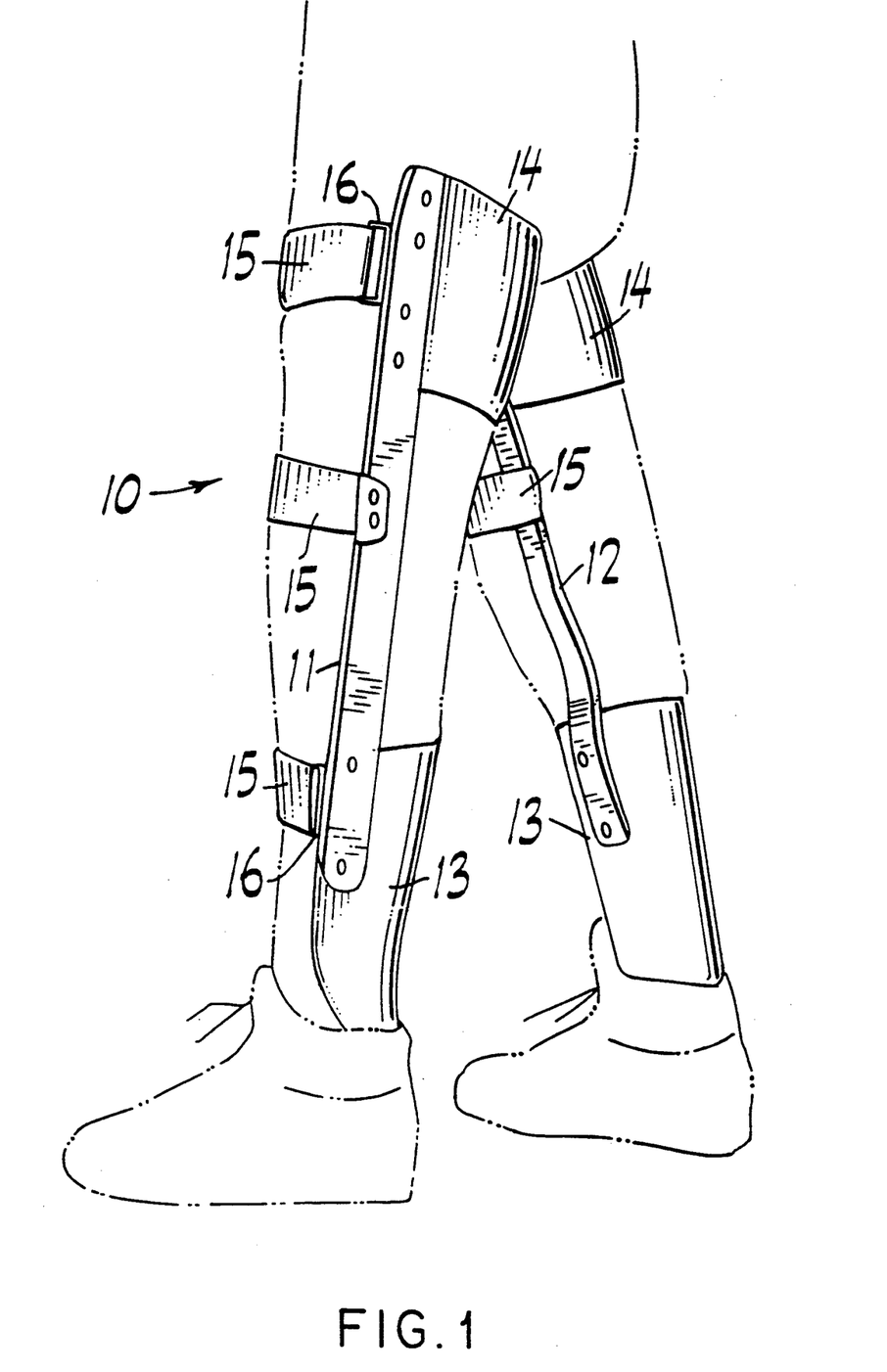
FIG. 1 is a pictorial illustration of one embodiment of the present invention.

With reference to FIG 1, one embodiment of the invention is illustrated therein and it will be seen to include a lower leg orthotic device generally designated by the reference number 10. The lower extremity orthotic device 10 includes, for each leg of the wearer, an outer side member 11 which in use is worn against the outer side portion of the user's leg and an inner side member 12 which in use is worn against the inner side portion of the user's leg. The side members are composed of a lightweight, thermoplastic polymeric material, which can be thermally molded, preferably corrugated polypropylene or glass-reinforced vinyl. The upper portions of both the inner side member 12 and the outer side member 11 are secured to a thigh cuff 14, which essentially wraps around the entire rear portion and part of both side portions of a wearer's upper thigh. Examples of securing means are nuts, bolts, or screws, which are inserted through the side members 12, 11, and thigh cuff 14 in holes drilled therethrough. The lower portions of both the inner and outer side members 12, 11, are secured to the upper portion and opposite sides of a custom fitted ankle foot orthosis 13, made of the same thermally moldable lightweight, polymeric material, preferably polypropylene or glass-reinforced vinyl and having corrugations introduced in specific portions thereof to increase rigidity Examples of securing means are screws, nuts, and bolts inserted in holes drilled through the lower portions of both side members 12, 11 and upper opposite sides of the ankle foot orthosis 13. The ankle foot orthosis is worn inside shoes chosen by the user. The thigh cuff 14, inner side member 12, outer side member 11, and ankle foot orthosis 13 are secured to the wearer's leg by fastening means in the form of straps 15 made of a flexible material, such as cloth, leather or the like. The straps are attached to the inner and outer side members 11, 12 by anterior strap attachments 16 which can be secured to the lateral edges of both the inner side member 12 and outer side member 11. Alternately, the anterior strap attachments 16 can be secured to the front edges of both side members 11, 12.

Figure 2:
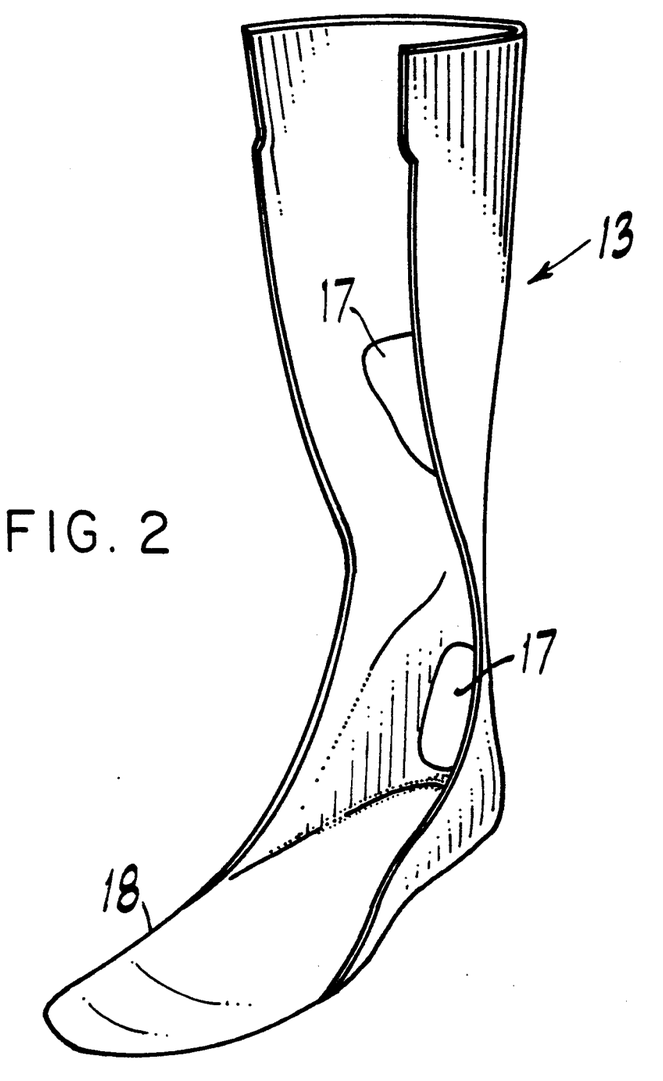
FIG. 2 is a pictorial illustration of an ankle foot orthosis used in the present invention.

FIG.2 shows the ankle foot orthosis 13 in greater detail. The method of fitting and casting an ankle foot orthosis has been previously described in Engen, Orthotics and Prosthetics 26 (4):1-15. There are two places in the ankle foot orthosis where the lightweight polymeric material is removed after casting. Removing the two areas renders a "cross" and two openings 17 at the posterior junction, just above the heel. These two openings 17 allow elasticity in the foot angle complex which can be fine tuned by cutting away more of the polymeric material to increase flexibility The sole portion 18 of the ankle foot orthosis 13 which was not visible in FIG.1 is visible in FIG.2. The sole of a user's foot is placed over the sole portion 18 of the ankle foot orthosis 13 and then inserted into a shoe of the user's choice.

Figure 3:
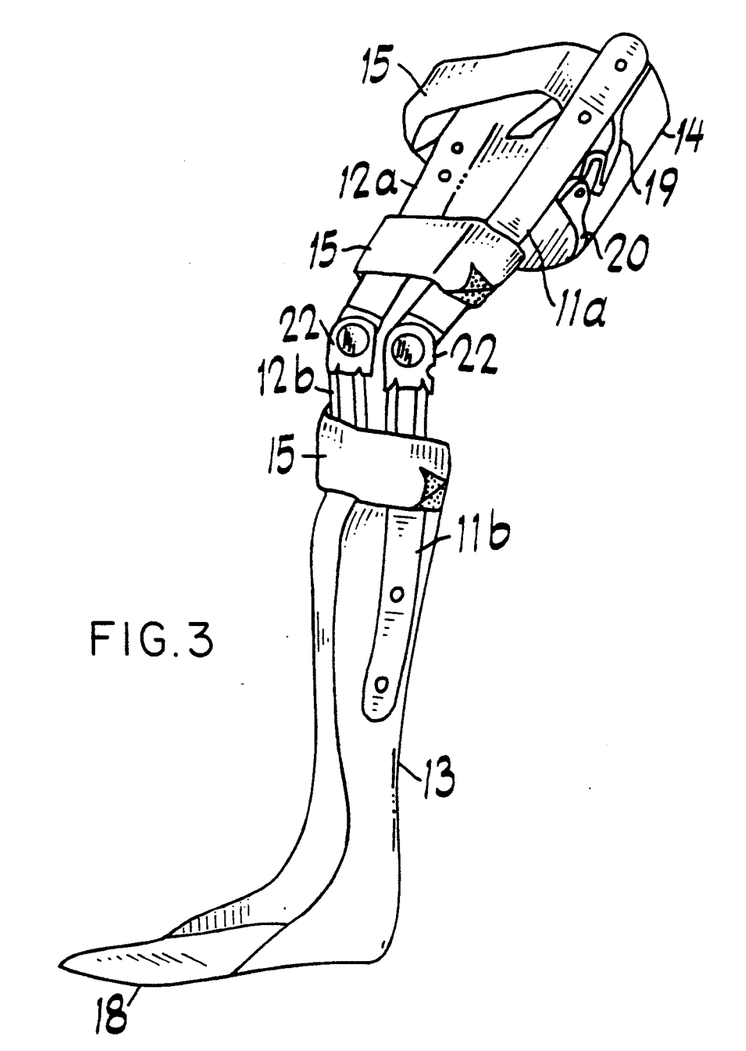
FIG. 3 is a pictorial illustration of a second, embodiment of the present invention.

FIG.3 shows another embodiment of the invention. In this aspect of the invention, a pair of knee joints 22 is introduced. A first knee joint 22 is interposed between an inner thigh side member 12a and an inner calf side member 12b. A second knee joint 22 is interposed between an outer thigh side member 11a and an outer calf side member 11b. For each leg of the user, means for maintaining the knee joint in a locked or unlocked position include a spring loaded cable mechanism, a hydraulic system or an electrical system. While these are not visible in FIG.3 since they are located inside longitudinal conduits in both the inner thigh side member 12a and the outer thigh side member 11a. The cable mechanism is discussed by way of exemplifying the invention. A first cable located within a conduit in the outer thigh side member 11a exits the outer thigh side member 11a via a hole drilled therethrough and enters a housing 20 which is secured to the lower edge of the thigh cuff 14. The housing 20 wraps around the user's thigh with the thigh cup 14 whereupon the cable then enters a conduit in the inner thigh side member 12a via a hole drilled therethrough. Inside the conduit located within the inner thigh side member 12a, the first cable is secured to a second cable. One end on both of the cables is joined to a conical shaped plunger which can move into and out of a hollow chamber located in the knee joint 22. Means for moving the plunger into or out of the knee joint 22 is supplied by a hand controlled lever 19 mounted on the thigh cuff 14. The hand controlled lever 19 is attached to the first cable. Since the first cable is attached to the second cable inside the inner thigh side member 12a, depressing the hand controlled lever 19 moves both cables out of the knee joints 22, thus allowing the inner calf side member 12b and outer calf side member 11b to rotate in relation to the inner and outer thigh side members 11a, 12a.

Figure 4:
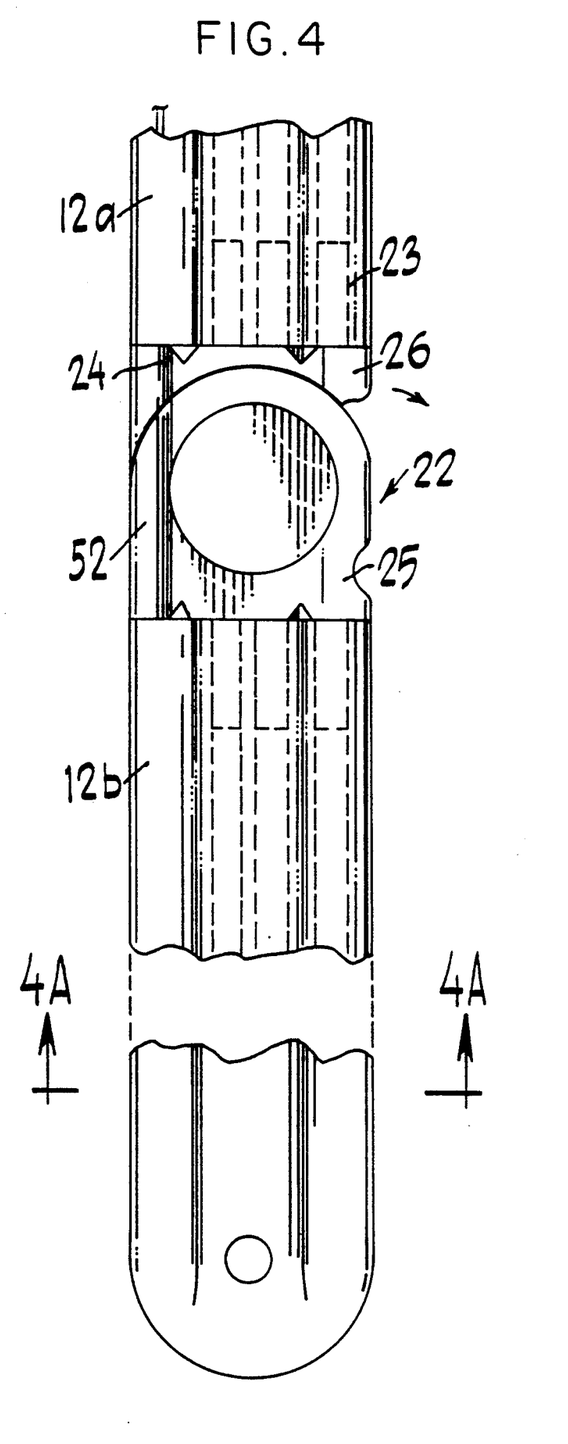
FIG. 4 is a front elevational view partly in section of a knee joint used in the embodiment of FIG. 3.

FIG.4 shows a knee joint 22 interposed between a thigh side member 12a and a calf side member 12b. The knee joint 22 has a plurality of threaded projections 23 on opposite ends which allow insertion into corresponding longitudinally disposed hollow conduits of both the thigh side member 12a and calf side member 12b. Knee joints 22 are each essentially composed of two halves, a first half 25 and a second half 26 which are secured to each other. The half 25 contains a hollow lower chamber 52 and the second half 26 contains a hollow upper chamber 24. When both the upper chamber 24 and lower chamber 52 remain hollow, the second half of the knee joint 26 can rotate in the direction of the arrow, a plunger attached to the cable enters the lower chamber 52 of the first half 51, after first entering the upper chamber 24 of the second half 26, the second half 26 of the knee joint 22 is prevented from rotating.

Figure 4A:
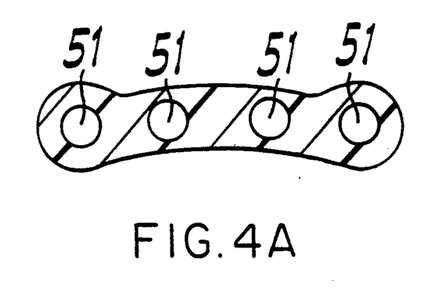

FIG.4a is a cross sectional view of a side member illustrating the plurality of hollow conduits 25 which confer lightweight properties and tortial rigidity to the side members and which can act as access ways for means to control the knee joint 22 via cables, electrical circuits, or tubing containing hydraulic fluid in the case of a hydraulic system.

Figure 5:
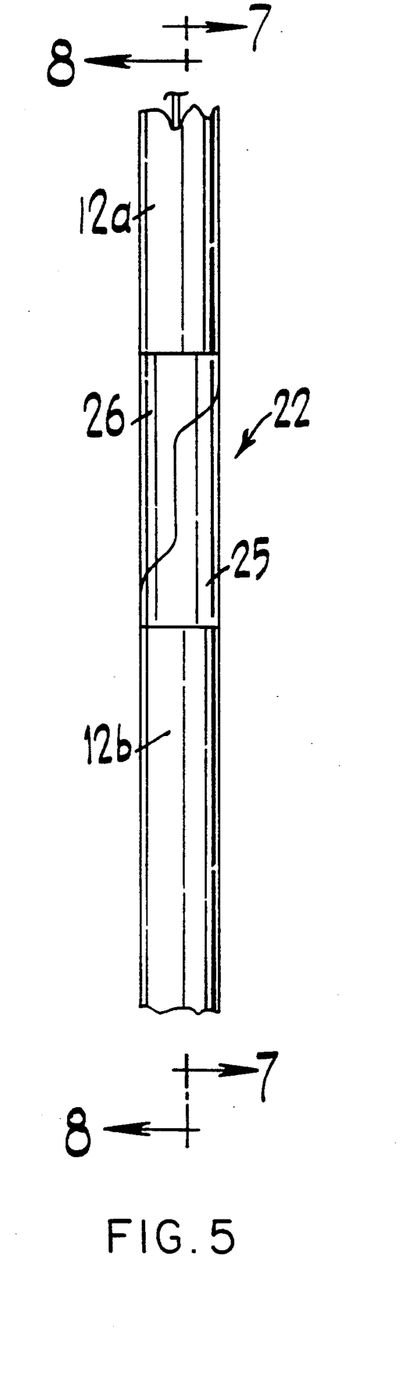
FIG. 5 is a side view of the knee joint shown in FIG. 4.

FIG.5 is a lateral view of the knee joint 22 interposed between a thigh side member 12a and calf side member 12b. Both the first half 25 and the second half 26 of the knee joint 22 are visible.

Figure 6:
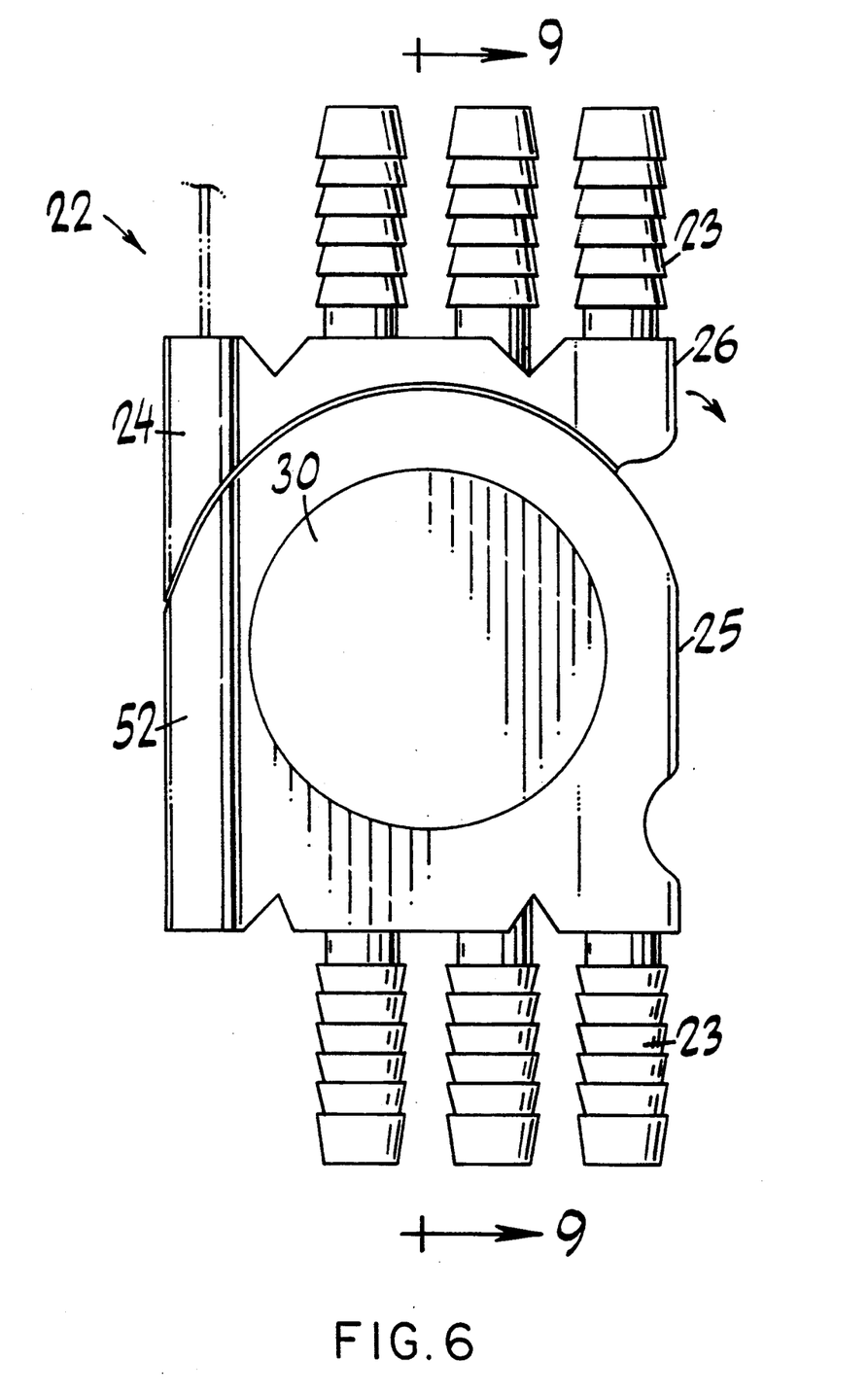
FIG. 6 is an exploded front elevational view of the knee joint shown in FIG. 4.
Figure 7:
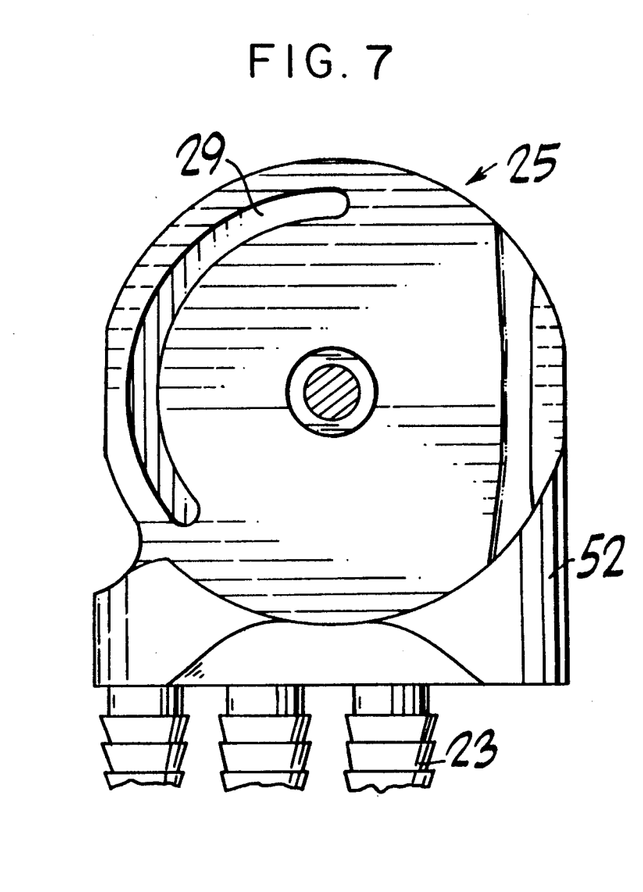
FIG. 7 is a front internal view showing one half of the knee joint of FIG. 4.
Figure 8:
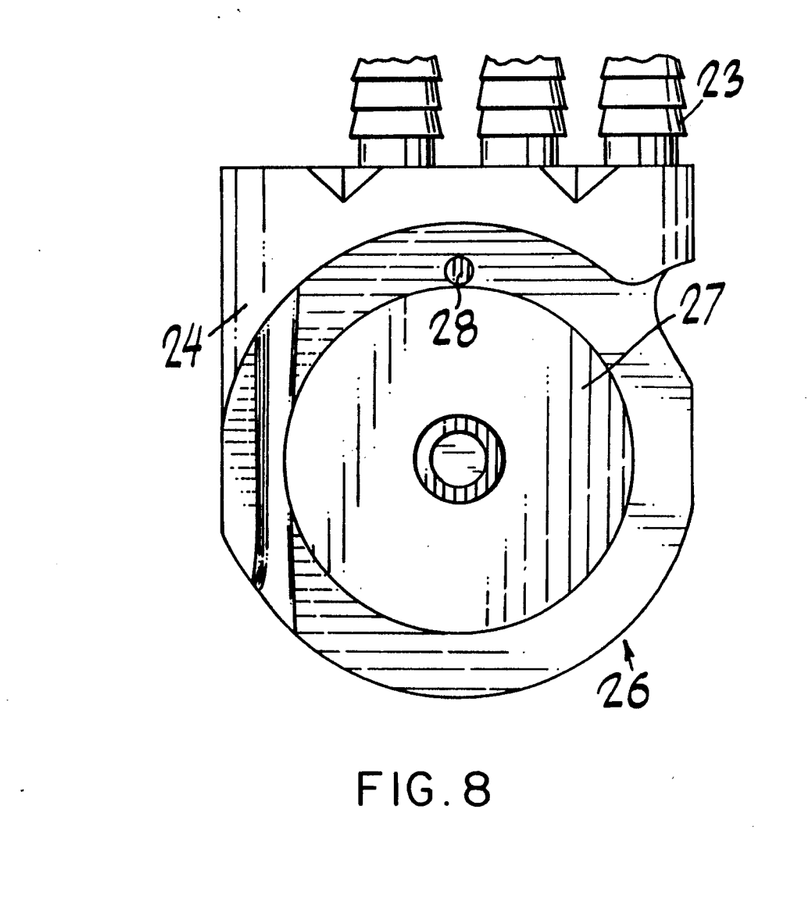
FIG. 8 is a front internal view showing a second half of the knee joint of FIG. 4.

FIG.6 is an exploded view of one of the knee joints 22. The joint 22 can be seen to consist of two halves, 25 and 26 which are shown in greater detail in FIG.7 and FIG.8. FIG.7 is an internal view of the first half 25 the knee joint 22, which shows the presence of a recess 29. FIG.8 shows a second half 26 of the knee joint 22. This second half 26 contains a follower 28 which fits into the recess 29 of the first half 25 when the two halves 25, 26 are put together. The fitting of the follower 28 of the second half 26 of the knee joint 22 into the recess 29 of the first half 25 the knee joint 22 allows the second half 26 to rotate in relation to the first half 25 of the knee joint 22. When the two halves 25,26 are in position, the exterior portion of the hollow chamber 24b of the first half 25 of the knee joint 22 acts as an anterior stop, and therefore prevents the second half of the knee joint 26 from rotating in a reverse direction than that illustrated by the arrow in FIG.6. A plastic disk 27 is contained within the second half 26 of the knee joint 22 and its function is to reduce friction on the two halves of the knee joint 22.

Figure 9:
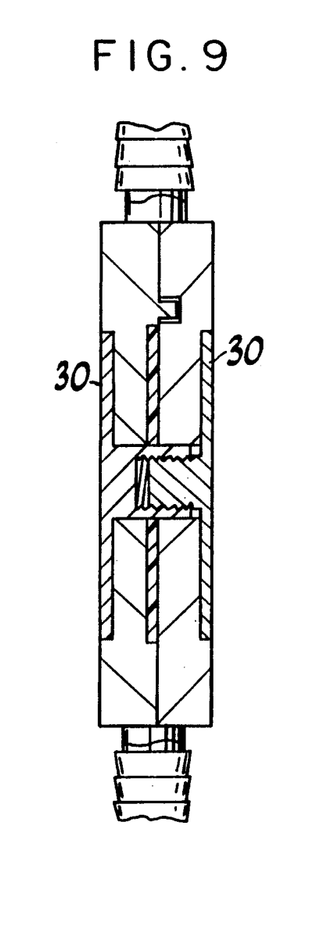
FIG. 9 is a cross-sectional side view of the knee joint of FIG. 6.

FIG.9 is a cross sectional view of the knee joint 22 as pictured in FIG.6. Once the two halves 25, 26 of the knee joint 22 are fitted together, they are secured by a pair of round covers 30. One round cover 30 is visible in the exploded view of the knee joint in FIG.6.

Figure 10:
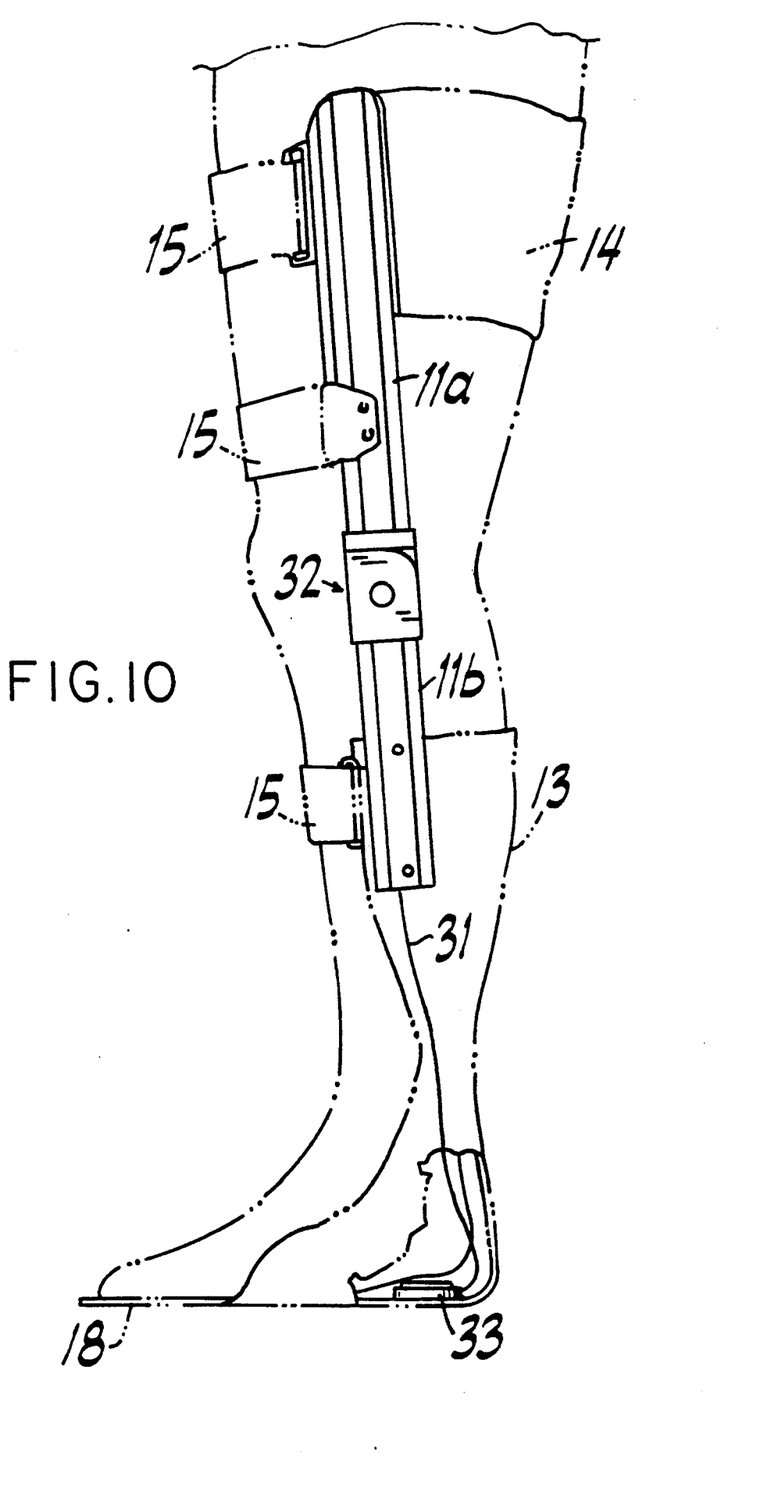
FIG. 10 is a pictorial view of a third embodiment of the invention.
Figure 11:
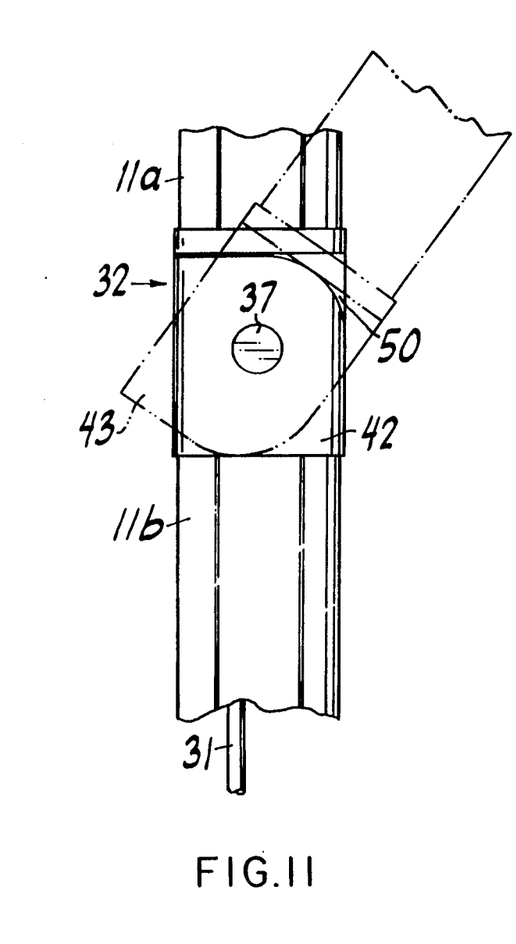
FIG. 11 is a front elevational view of a knee joint used in the embodiment of FIG. 10.
Figure 12:
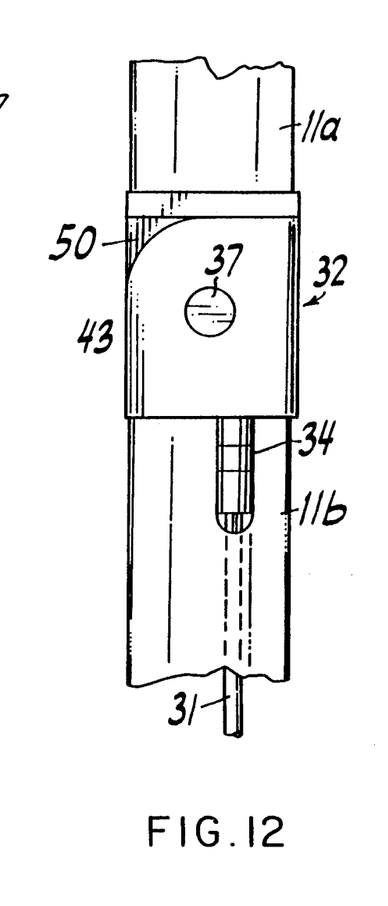
FIG. 12 is a back elevational view of the knee joint shown in FIG. 11.

FIG.10 is a view of one aspect of the invention where the means to control the knee joint comprises a hydraulic system. Plastic tubing 31 is used to hold the hydraulic fluid. A heel chamber 33 containing a piston is inserted on top of the heel portion of the ankle foot orthosis 13. The body weight of the user is transferred to the chamber 33 when the user's heel rests on top of the chamber 33. This pressure controls the movement of the hydraulic fluid through tubing 31. The hydraulic tubing runs through the hollow conduit 25 longitudinally disposed within the calf side member 11b. A knee joint 32 is interposed between the thigh side members 11a,12a and the calf side members 11b, 12b. FIG.11 and FIG.12 show enlarged views of the knee joint 32 employed with the hydraulic system. The knee joint 32 is comprised of two halves, a first half 42, a second half 43 and an inner body 50. FIG.11 shows the rotation of the second half 43 of the knee joint 32 in relation to the first half 42 of the knee joint 32 and the interposition of the knee joint 32 between a thigh side member 11a and calf side member 11b. FIG.12 shows a partial view of a conical shaped plunger 34 which is attached to the end of the plastic tubing 31 and which is normally positioned inside a hollow chamber of the knee joint 32 and prevents the rotation of the first half 42 and the second half 43 in relation to each other.

Figure 13:
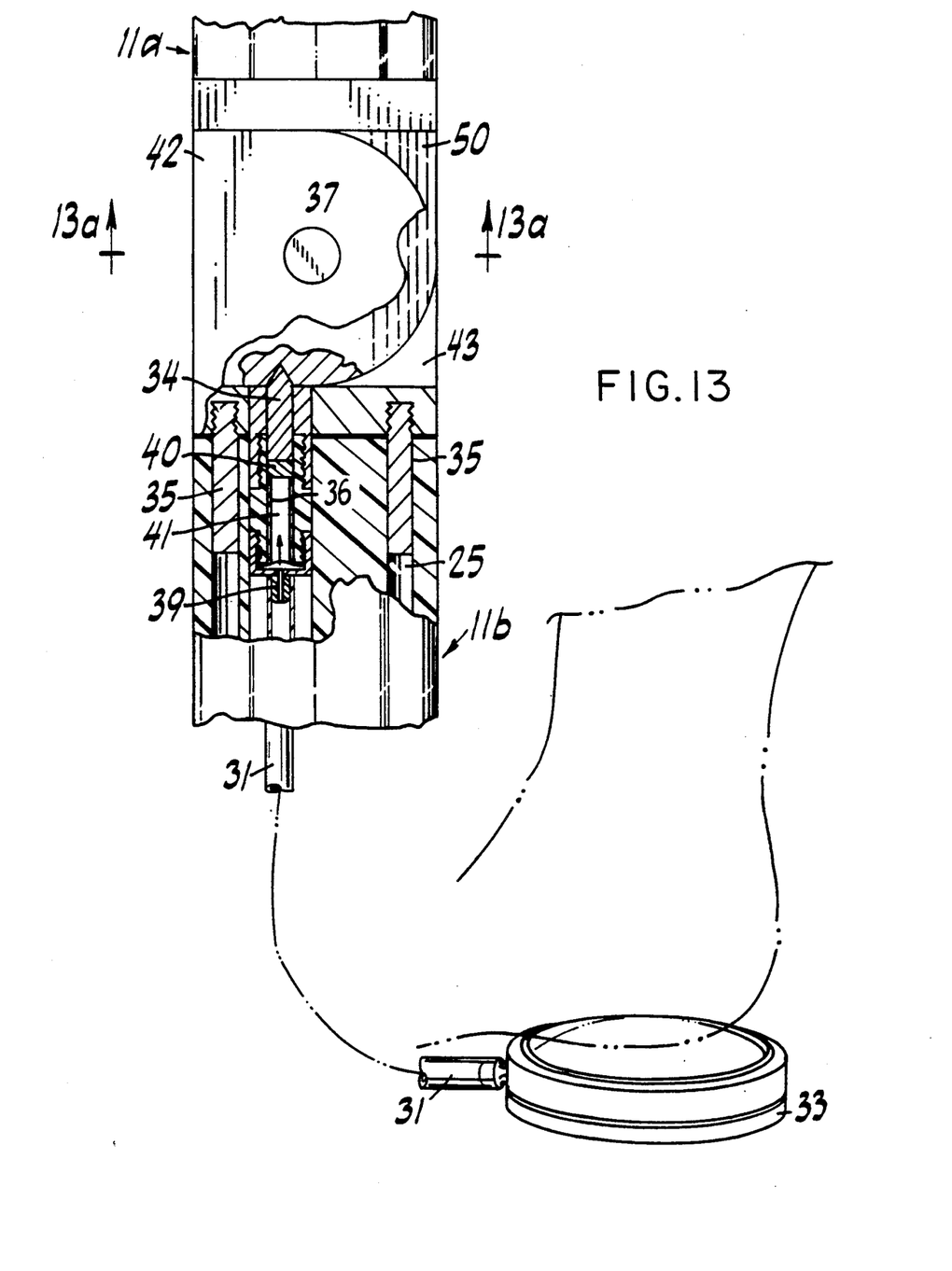
FIG. 13 is a front internal view partly in section of a knee joint in a locked position attached to a side member as used in the embodiment shown in FIG. 10.

FIG.13 is a cutaway view of FIG.11 showing the internal mechanism of the hydraulic system and knee joint 32. It can be seen that pressure in the hydraulic fluid contained in the tubing 31 is created by the user pressing his or her heel down on the heel chamber 33 At the end of the tubing 31 contained within the calf side member 11b is a fitting 39 which presses up against a rubber sheath 36. The rubber sheath 36 is secured to the base of the plunger 34 by a small cap 40. When there is pressure in the hydraulic fluid contained within the tubing 31 as when the wearer is depressing the heel chamber 24, the rubber sheath expands, thereby pushing the plunger 33 up into the hollow chamber 41 contained within the knee joint 32. In this position, the physical presence of the plunger 34 prevents the second half 43 of the knee joint 32 from rotating. A pin 37 secures the two halves of the knee joint 32 to the knee joint body 50. A pair of posts 35 which are threaded on one end are inserted via their unthreaded ends into hollow conduits in the calf side member 11b and have their threaded ends inserted into the knee joint 32 to hold the knee joint 32 secure to the calf side member 11b.

Figures 13A, 14:
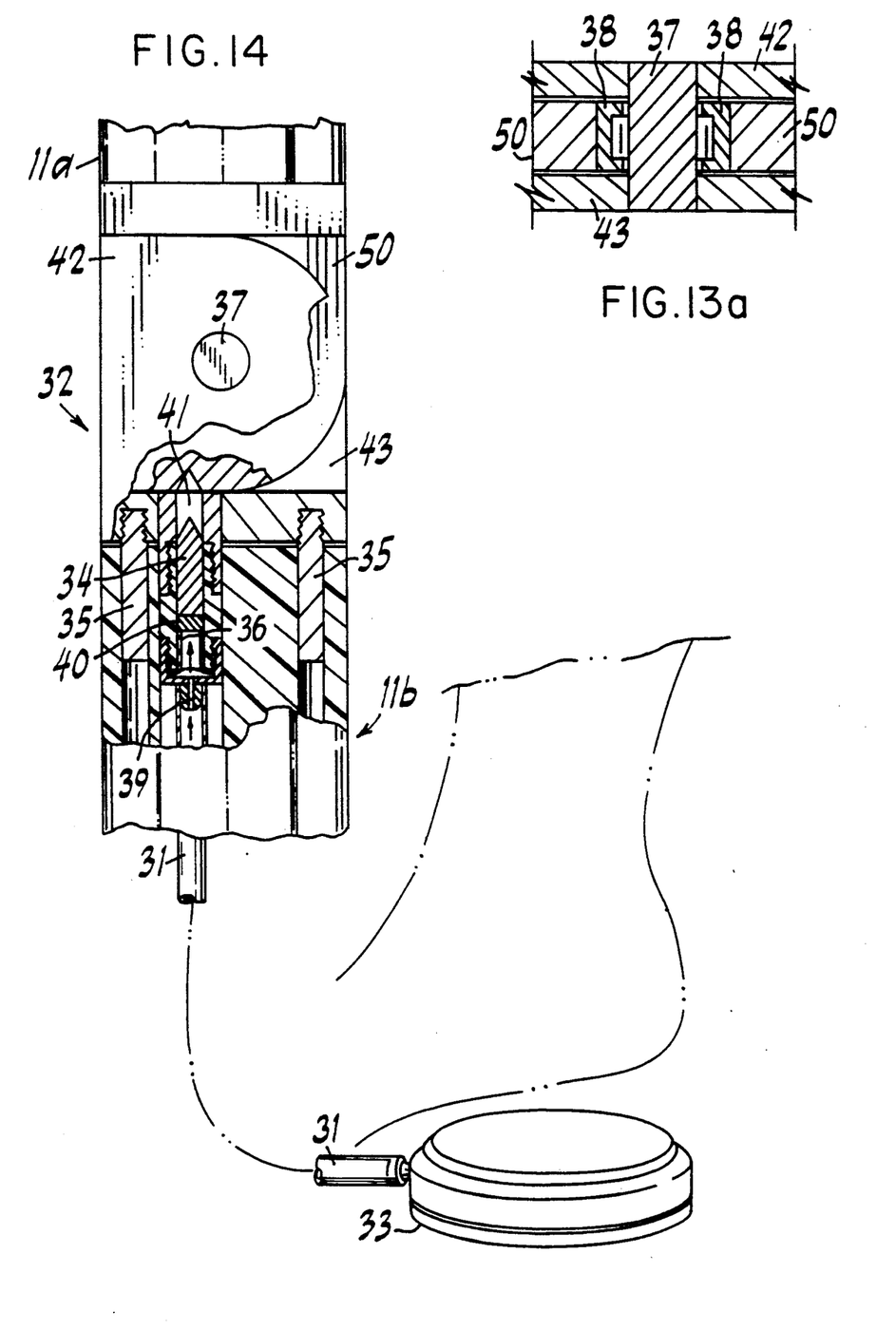

FIG.13a is a cross sectional view of the knee joint 32. Pin 37 secures both halves 42,43 of the knee joint 32 to the knee joint body 50. A set of bearings 38 surrounds the pin 37 and serves to reduce friction on the pin 37 and both halves 42,43 of the knee joint when the first half 42 rotates in relation to the second half 43.

FIG.14 shows the same view of the knee joint 32 and hydraulic system when the user's heel is removed from the heel chamber 33 which causes the pressure in the hydraulic fluid within the plastic tube 31 to be removed. This release in pressure on the hydraulic fluid releases the pressure of the fitting 39 which in turn releases the pressure on the elastic rubber sheath 36. When the pressure is released from the rubber sheath 36, the sheath 36 returns to its unexpanded state and the plunger 34 is allowed to move out of the hollow chamber 41. The removal of the plunger 34 from the hollow chamber 41 acts to unlock the knee joint 32. As a result, the two halves 42, 43 of the joint 32 are allowed to rotate in relation to the knee joint body 50 as illustrated in FIG.11, thus allowing the thigh side member 11a to rotate in relation to the calf side member 11b.

Figure 15:
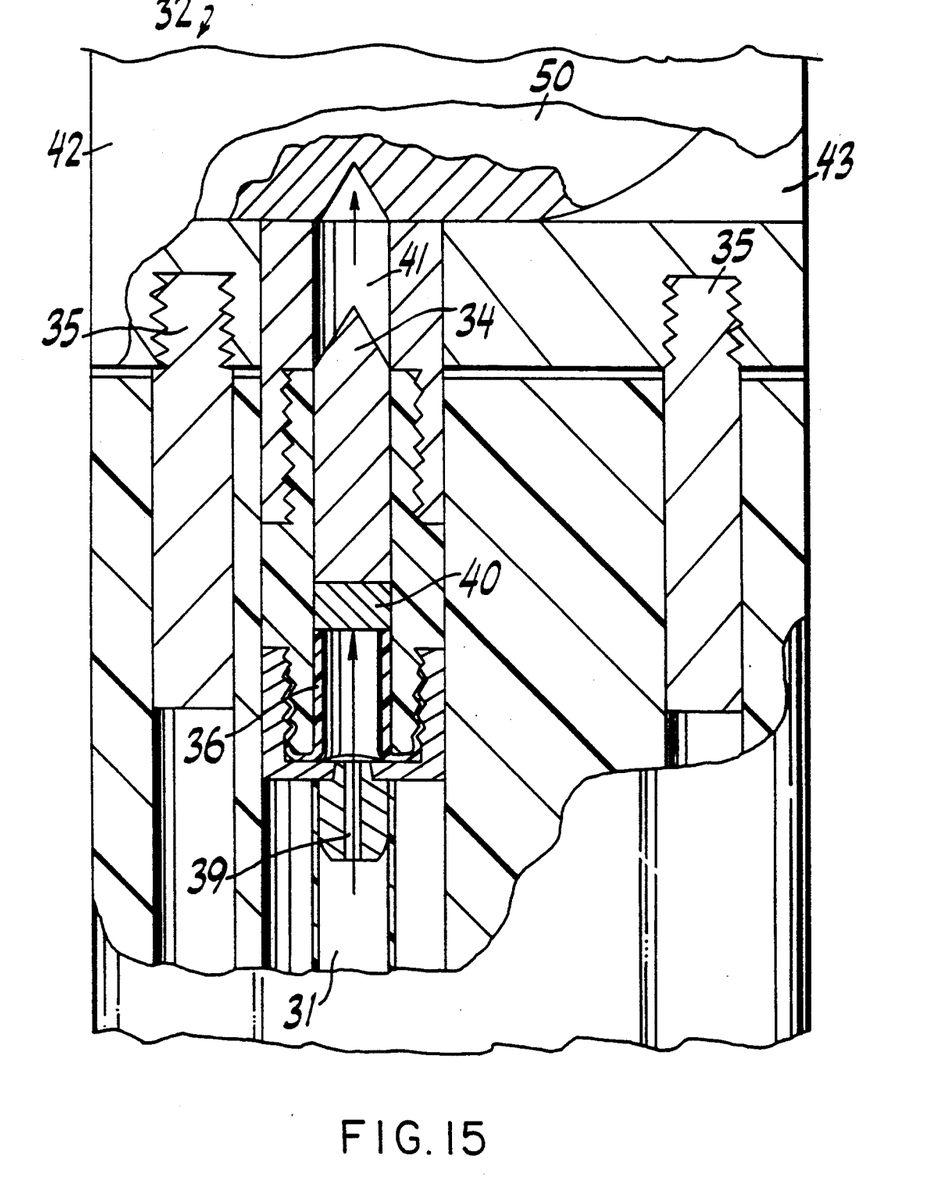
FIG. 15 is an exploded view of the knee joint shown in FIG. 14.

FIG.15 is an exploded view of the lower portion of the knee joint 32 and part of the calf side member 11b. In this figure, the plunger 34 is removed from the hollow chamber 41, and the joint is unlocked, in position for the two halves 42,43 to rotate in relation to the knee joint body 50.

The knee joint control means can also be made to operate under control of an electronic circuit. The chamber 32 of FIGS. 10–14 can be adapted to house an electrical switch as an alternative to the piston device described hereinabove. The switch acts to provide an electrical signal to an electronic control circuit housed in knee joint 32 via an electrical conductor supplied from the chamber 33 to the circuit through the hollow conduit 25 contained in calf side member 11b. The electrical control signal will typically be at one of two voltage levels, each level corresponding to the state of the switch in chamber 33, which state will correspond to the position of the heel upon the chamber 33.

In accordance with known principles, the plunger mechanism 34 is adapted to be responsive to the electronic control circuit which will act to push the plunger 34 up into the chamber 41 to thereby lock the knee joint in response to pressure exerted upon the switch in chamber 33. In this manner, the knee joint mechanism is controlled in much the same way as with the use of the hydraulic system described hereinabove.

The detailed description of the invention having been set forth herein, it is known that there can be departure from the embodiments described without departing from the true scope of the invention.

What is claimed is:

1. A lower extremity orthotic device comprising unitary inner and outer side members made of a lightweight thermoplastic material; a plurality of hollow conduits running longitudinally within each of the side members; each of the side members having a slightly curvilinear cross section which has a first-dimensioned inner portion which is at least as large as the cross section of one of the plurality of hollow conduits and a second-dimensioned outer portion located near the lateral edges of the side members and being slightly larger than the first-dimensioned inner portion, the side members being adaptable to accept knee joint means, the plurality of hollow conduits providing the device with lightness and rigidity to support weight bearing axial and torsional loads, a thigh cuff member disposed so as to wrap around at least a portion of a wearer's thigh; and a custom fitted calf-ankle-foot orthotic member wherein one end of each of the side members is secured to the thigh cuff, a second opposite end of each of the side members is secured to the calf-ankle-foot orthotic member, and each of the side members being provided with fastening means for securing the side members and the calf-ankle-foot orthotic member against the wearer's leg.

2. A lower extremity orthotic device comprising unitary inner and outer thigh side members; unitary inner and outer calf side members; all of the side members composed of a lightweight thermoplastic material, a plurality of hollow conduits running longitudinally within each of the side members; each of the side members having a slightly curvilinear cross section which has a first-dimensioned inner portion which is at least as large as the cross section of one of the plurality of hollow conduits and a second-dimensioned outer portion located near the lateral edges of the side members and being slightly larger than the first-dimensioned inner portion, knee joint means interposed between the thigh and calf inner and outer side members; the knee joint means having projections on opposite ends thereof which fit within one or more of the hollow conduits exposed at cross sections of the thigh and calf side members, means for maintaining the knee joint means in a locked or unlocked position; the plurality of hollow conduits in addition providing the device with access ways for housing and protecting the means to maintain the knee joint means in a locked or unlocked position, and also providing the device with lightness and rigidity to support weight bearing axial and torsional loads, a thigh cuff member disposed so as to wrap around at least a portion of the wearer's thigh; and a custom fitted calf-ankle-foot orthotic member, wherein one end of each of the inner and outer calf side members is secured to the calf-ankle-foot orthotic member, and a second opposite end of each of the inner and outer calf side members is secured to one end of the knee joint means, and wherein one end of each of the inner and outer thigh side members is secured to the thigh cuff and a second opposite end of each of the inner and outer thigh side members is secured to a second opposite end of the knee joint means, and each of the inner and outer thigh and calf side members being provided with fastening means for securing the thigh side members, the calf side members, and the calf-ankle-foot-orthotic member against the wearer's leg and wherein the knee joint means in an unlocked position allow the thigh and calf inner and outer side members to rotate in relation to each other.

3. A lower extremity orthotic device according to claim 1 or 2 wherein the lightweight, thermoplastic material is polypropylene.

4. A lower extremity orthotic device according to claim 1 or 2 wherein the lightweight, thermoplastic material is glass-reinforced vinyl.

5. A lower extremity orthotic device according to claim 2 wherein the means for maintaining the knee joint in a locked or unlocked position comprises a cable system.

6. A lower extremity orthotic device according to claim 2 wherein the means for maintaining the knee joint means in a locked or unlocked position comprises a hydraulic system and hydraulic tubing disposed within one or more of the hollow conduits.

7. A lower extremity orthotic device according to claim 2 wherein the means for maintaining the knee joint in a locked or unlocked position comprises an electrical system.

8. A lower extremity orthotic device according to claim 5 wherein the means for maintaining the knee joint in a locked or unlocked position further comprises a plurality of cables, a plunger attached at one end of each of the cables, a cable housing secured to and wrapping around the outside of the thigh cuff, and a hand controlled lever secured to the thigh cuff, wherein a first cable is disposed inside a hollow conduit longitudinally running through the outer thigh side member and having the plunger-end of the cable inserted inside the center of the knee joint, thereby preventing the knee joint from rotating, and a second cable disposed inside a hollow conduit longitudinally running through the inner thigh side member and having the plungerend of the second cable also inserted inside the center of the knee joint, the first cable exiting the outer thigh side member by means of a hole drilled therethrough, the cable then running through the cable housing, entering the inner thigh side member by means of a hole drilled therethrough, and attaching to the cable contained within the inner thigh side member, so that when the hand lever is depressed, the plungers attached at one end of each of the cables displace from the center of the knee joints, thereby unlocking the joints.

9. A lower extremity orthotic device according to claim 8 further comprising a spring added to each of the plunger ends of the first and second cables.

10. A lower extremity orthotic device according to claim 6 wherein the means for maintaining the knee joint means in a locked or unlocked position further comprises a chamber member disposed below the heel portion of the calf-ankle-foot orthotic member and being insertable into the insole portion of a wearer's shoe; the chamber member having a piston therein which is adapted to respond to pressure exerted by the user for controlling the movement of hydraulic fluid contained in the hydraulic system, the hydraulic fluid being in mechanical contact with a plunger disposed in the center of the knee joint means and exerting pressure on the plunger to maintain it in the center position when pressure is exerted on the piston to lock the knee joint means and to allow the plunger to retreat from the center position when pressure exerted on the piston is relieved, to unlock the knee joint means such that the thigh and calf inner and outer side members can rotate in relation to each other.

11. A lower extremity orthotic device according to claim 7 wherein the means for maintaining the knee joint in a locked or unlocked position further comprises a chamber member disposed in the heel of the calf-ankle-foot orthotic member having a switch therein which is adapted to respond to pressure exerted by the user for supplying a control signal along conductor means disposed in a hollow longitudinal conduit of one of the inner and outer side members to an electromechanical control circuit which is adapted to control plunger disposed in the center of the knee joint by exerting pressure on the plunger to maintain it in the center position when pressure is exerted on said switch to thereby prevent said knee joint from rotating and to allow said plunger to retreat from the center position When pressure exerted on said switch is relieved, to thereby allow said knee joint to rotate 12. A lower extremity orthotic device according to claim 1 or 2 wherein the cross section of each of the side members has a shape as shown in FIG. 4A.

* * * * *